United States Patent [19]
Chiquiar-Arias

[11] 3,951,146
[45] Apr. 20, 1976

[54] DISPOSABLE SELF-DESTRUCTIBLE SYRINGES WHICH RENDER THEMSELVES UNREUSABLE

[76] Inventor: Marcelo Chiquiar-Arias, Insurgentes sur 403-5, Mexico City 11, Mexico

[22] Filed: May 29, 1974

[21] Appl. No.: 474,283

Related U.S. Application Data

[63] Continuation-in-part of Ser. No. 302,690, Nov. 1, 1972, abandoned.

[30] Foreign Application Priority Data

Aug. 15, 1973  Mexico .................................. 145570

[52] U.S. Cl............................ 128/218 R; 128/218 P; 128/218 PA
[51] Int. Cl.² .......................................... A61M 5/00
[58] Field of Search ............ 128/215, 218 R, 218 P, 128/218 C, 218 PA, 234, 261; 222/541; 401/198; 30/90.4, 90.1, 123 R; 206/365

[56] References Cited
UNITED STATES PATENTS

| | | | |
|---|---|---|---|
| 2,619,087 | 11/1952 | Oclassen ........................ | 128/234 X |
| 2,724,385 | 11/1955 | Lockhart ........................ | 128/234 X |
| 2,752,920 | 7/1956 | Kurkjian ............................ | 128/261 |
| 2,764,981 | 10/1956 | Helmer et al. ................... | 128/218 C |
| 2,833,280 | 5/1958 | Hein, Jr. .......................... | 128/218 D |
| 2,882,899 | 4/1959 | Nogier et al..................... | 128/218 P |
| 3,220,413 | 11/1965 | Sunnen .............................. | 128/261 |
| 3,667,657 | 6/1972 | Chiquiar-Arias............. | 128/218 R X |

FOREIGN PATENTS OR APPLICATIONS

| | | | |
|---|---|---|---|
| 107,080 | 4/1971 | Mexico | |
| 1,257,067 | 2/1961 | France............................. | 128/218 P |
| 268,694 | 5/1951 | Switzerland..................... | 128/218 P |

*Primary Examiner*—John D. Yasko
*Attorney, Agent, or Firm*—Ladas, Parry, Von Gehr, Goldsmith & Deschamps

[57] ABSTRACT

This invention refers to disposable syringe containers used for injection which destroy themselves and render themselves unreusable, characterized principally in that they are made of a material which can be cut with the normal injecting movement of the piston in the syringe, thus destroying them.

6 Claims, 12 Drawing Figures

U.S. Patent April 20, 1976 3,951,146
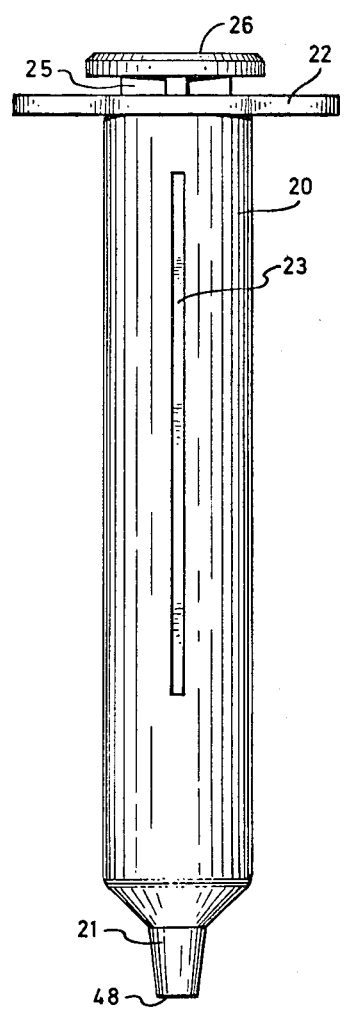
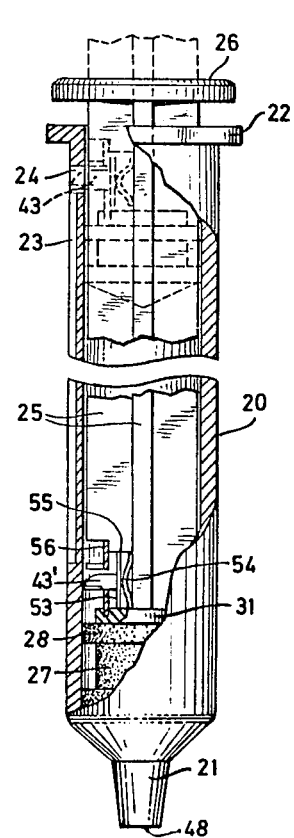
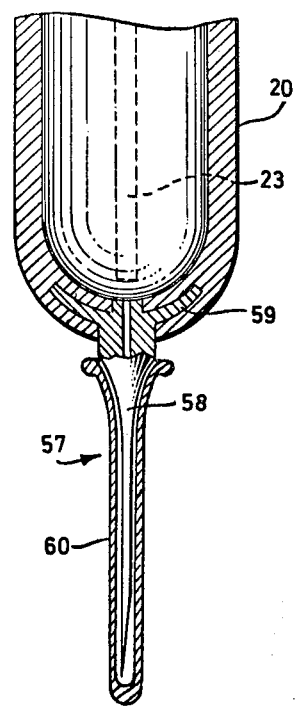
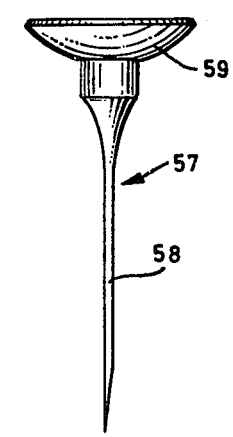

DISPOSABLE SELF-DESTRUCTIBLE SYRINGES WHICH RENDER THEMSELVES UNREUSABLE

REFERENCES TO OTHER APPLICATION

The present application is a continuation-in-part of my Pat. application Ser. No. 302,690, filed on Nov. 1, 1972 now abandoned.

BACKGROUND OF THE INVENTION

This invention is designed to solve not only the problem of preventing contamination caused by disposable syringes if they are reused by the users, since this is a current problem of world interest, this problem is completely solved with the syringes which render themselves unreusable, which are the subject of the aforementioned Patent Application, but this invention also provides the solution to the problem of the possible reuse of syringes by drug addicts, a problem which was not completely solved with the aforementioned syringes which rendered themselves unreusable.

The improvements set forth in this invention make the use of the syringes more effective and easier and prevent their possible reuse, even in a partial manner, as well as preventing the possible reuse of the injection needle. The aforementioned syringes could have their needles reused inasmuch as regular needles were used. For this reason, one of the aspects of this invention is to prevent the possible reuse of the needles.

My U.S. Pat. No. 3,667,657 shows a pre-filled syringe in which a non-retractable knife destroys the syringe on use. There are some injectable solutions which cannot be stored for a given amount of time in containers made of material which can be cut with a blade, such as plastic or similar materials. For this reason there is a necessity for a syringe for these types of solutions which can be filled without the blade cutting the cylinder at the time that the solution is extracted from its container in the process of filling the syringe. My Mexican Pat. No. 107,080 shows attaching a resiliently mounted knife to one of the sides of the flaps of the piston rod. However, in this fashion the resiliently mounted knife does not move radially of the piston rod and does not squarely strike the inner surface of the cylinder of the syringe, resulting in a difficult and imprecise cutting action. It is an object of this aspect of the invention that the cutting blade be operated most efficiently so as to permit cutting of the syringe with the minimum additional force required by the user and with maximum reliability in operation.

In accordance with one aspect of the invention the cutting blade is supported on the piston rod by a resilient mounting so that said knife moves radially of the central axis of the cylinder and thus squarely meets the interior surface of the cylinder of the syringe. The knife cuts a half-groove weakening extending longitudinally of the cylinder of the piston after first passing through a full groove or a deepened groove at one end of the half-groove. In a preferred embodiment of the invention the movement of the knife is controlled by guiding means also affixed to the piston rod, such as a slotted plate, which keeps the knife in a plane passing through the central axis of the cylinder. In this way the position of the knife, which is generally planar, is maintained in a position properly to cut the inner surface of the cylinder. The slotted plate also insures that the knife passes outwardly through the full slot in the cylinder when the piston is brought into its retracted position during the aspiration of the syringe with the injecting fluid.

By placing the compressible cutting blade within a recess in one of the flaps of the plunger of the syringe or in an integral seat in said plunger, one also simplifies the manufacture of the syringe and allows uniform pressure during the cutting.

Manufacture is simplified since the weakening of the outside of the cylinder does not have to be outside of the diametrically opposed point of the stops which function as guides for the flaps of the plunger, but it may coincide with said diametrically opposed point generally the entire length of the cylinder.

One embodiment of the invention consists of a blade supported by a laminated or other type spring located in the stated slot and which allows the placing of the blade inside said stated seat in the flap of the plunger. This model may be used in empty syringes in which the blade, during the filling or aspiration process, which is to say, during the time that the plunger is removed to its outermost position, will not cut the cylinder because the outer edge is rounded and does not cut, but, nevertheless, when the plunger has been removed a certain distance which corresponds to a determined dose, the blade will come out radially of an opening or slot made in the cylinder which coincides with the end of the groove or weakened section on the outside of the cylinder because of the force exerted by the spring to which it is connected. Rather than the opening crossing the entire wall of the cylinder of the syringe, it could be only a small hollow space which does not extend to the outside surface, forming a step at practically the same height as the space of the longitudinally weakened section of the cylinder in order to prevent the user from introducing any device from the outside, pushing in the blade and reusing the syringe. Upon injecting the solution contained in the syringe, the blade will cut the cylinder radially at the weakened section, thus, destroying the syringe and preventing any further use of it.

Another embodiment of the invention, principally for empty syringes, has a small seat, preferably tubular, located transversely to the axis of the plunger and beyond the disk which supports the piston in which is located a blade connected on one extreme end to a spring located inside the aforementioned seat; this blade has the side opposite the pivot rounded and the other side has a cutting edge and which includes guiding means like a cover of the said seat which also includes a slot with dimensions just slightly larger than the width of the blade which gives it a little play, which, when the plunger is extracted, due to the play of the blade, the same will not cut said cylinder since it moves along the inside of the cylinder, making contact with its rounded edge.

If, at any time during the movement of the plunger in filling the syringe, it is desired to inject the solution, due to the play of the blade, the latter will make contact with the inside of the cylinder with the cutting edge, cutting the wall of the cylinder across a weakened section made by a longitudinal slot outside the cylinder, which is to say, that in this model of the invention, the blade will cut provided that the piston moves toward the needle, i.e., that operation which is properly called injection, irrespective of whether or not the blade is at the end of the movement of the plunger or not, or in any position in between.

Of course, at the end of the groove or weakened longitudinal section, there is placed in the same manner a slot which runs all the way across the cylinder and allows for the exit of the blade through said slot to such a position that allows for the most ideal and simple cutting, destroying and rendering of the syringe unusable again.

For the total introduction of the plunger in this embodiment of the invention, without having the blade cut the cylinder; in the manufacture or assembly process of this syringe a thin spacing sheet is placed between the blade and the inside wall of the cylinder, which will be extracted once the plunger reaches the end of its movement in the area of the pivot of the syringe.

Still another purpose of this invention is to provide in an embodiment of same, a needle which will be nonreusable, which is to say, that it will not be adaptable to another type of syringe and which is incorporated in the same molding or manufacturing operation of the cylinder of the syringe at the end corresponding to the pivot, which this embodiment does not have since it is made up by the same needle.

This special needle which cannot be used on another type of syringe could be, on another model of this invention, integrally made with a positioning socket which could be applied to the extreme end of the cylinder of one of the disposable syringes, subject of this invention, including the syringe container which has a breakable end and over the cylinder the socket of the aforementioned integral needle can be placed.

In view of the fact that in most of the foregoing embodiments, drug addicts can refill, even with a small amount of solution, the destroyed syringe due to the small part of the syringe which is not cut and which corresponds to the size of the piston of the plunger, this invention furthermore includes the following aspects that solves this and other problems.

One of the embodiments of this aspect of the invention, has in the forward part of the piston, a needle or pin which coincides with a weakened position or groove made in the forward part of the cylinder without fully puncturing the wall of the same, in which case, when the solution is injected by the user and the piston reaches the end of its movement, the cylinder will be fully punctured in the said weakened section, preventing a possible reuse, however small it might be, of the syringe inasmuch as the syringe will be completely unusable. Of course this kind of destruction could be combined with the cutting blade which is outlined in the above models.

Another embodiment which solves the last problem mentioned above, has in the center and in the forward part of the piston a ribbed and toothed projection, or any other kind of mechanism which would jam when inserted into the needle on the first application of the solution, and it would stick in the ribbed part of the needle with which it would coincide, jamming the plunger with the needle, making any further reuse impossible. This embodiment could also be combined with the cutting blade as in the foregoing aspect and would include a stop near the extreme end of the cylinder of the syringe container in order to prevent destruction of the syringe when being assembled before the first application, preventing the pin and the jamming mechanism from making the syringe unworkable prematurely.

Yet another embodiment of this invention is applicable to the syringe container which is prefilled with an injectable solution and which may be manufactured in glass, in plastic, or in a combination of glass and plastic, for the plunger or the cylinder of the syringe, it would include some ledges serving as stops on the inside of the cylinder produced by simple pressure on the cylinder from the outside which would function as gaskets against a ratchet or stop located in a seat adjacent to the detention disk of the piston.

The mentioned stop would be guided by a slotted cover of the seat and forced by the working of a spring to which it would be hooked, located inside said seat and connected at its extreme end to the bottom of the same, so that, once the solution is injected, the stop which has its extreme end rounded and backside straight in relation to the bottom of the cylinder, would work against the gaskets pressed into the cylinder, preventing the possibility of returning the plunger once it has moved in the operation of injection. All of the aforementioned stops of this invention could be simply pressed into the cylinder in order to produce a raised section inside or stop in the same and which could be done by means of automatic molds, thermic or any other procedure.

These and other objectives to be obtained for the use of this invention will be better understood and appreciated by the reading of the following description which refers to the drawings of the preferred embodiment of the present invention.

BRIEF DESCRIPTION OF THE DRAWINGS

FIG. 1 is a vertical elevational view of a model of one embodiment of the invention for disposable or empty syringes with cutting blades elastically supported by springs located on the inside of the slots made in one flap of the plunger of the syringe.

FIG. 2 is a partial sectional view which illustrates the embodiment of the invention shown in FIG. 1, indicating with dotted lines, the position of the blade and the plunger when extracted from the cylinder in order to fill the syringe with solution to be injected.

FIG. 11 is a conventional longitudinal partial sectional view showing a disposable needle embedded in the bottom wall of the cylinder of the disposable syringe of this invention, indicated by dotted lines, the weakened sections of the cylinder of the syringes and including a covering protection for the needle.

FIG. 12 is a top elevational view of the needle shown in FIG. 11 before entering the cylinder of the syringe.

DETAILED DESCRIPTION OF THE INVENTION

Figure 3:
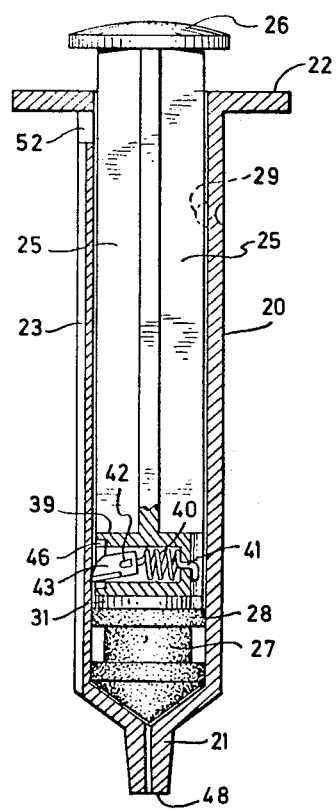
FIG. 3 is a conventional longitudinal sectional view which shows a modification of the embodiment shown in FIG. 2, having a blade elastically supported.

As related to the Figures, the improved syringe which is the subject of this invention is constructed according to the embodiments illustrated in FIGS. 1 to 18, with a cylinder 20 made of a material which can be cut by a knife, such as plastic or some similar material, and which has at one of its extreme ends a pivot 21 and at the other, projecting itself perpendicularly from its longitudinal axis, a pair of flanges 22, almost opposite, which function as supports for the user; cylinder 20, also includes a slot or longitudinally weakened section 23 on the inside of the cylinder 20, almost the whole length of the cylinder; the weakened portion 23, has at its extreme end which is nearest the flanges 22, a punctured portion 24, almost of the same width as the said slot 23, and which penetrates the entire wall of said cylinder 20.

The plunger of the syringe has some flaps 25 which are practically in the shape of a cross. At one of its extreme ends the plunger has a circular disk 26 and at its other extreme end a piston 27 with some annular sealing bosses 28.

Said cylinder 20 has in its inside surface some protuberance 29, which may be formed by simple pressure applied to the outside wall of the cylinder with a hot punch which will form the desired ledge which will act as a stop against one of the annular sealing bosses 28, limiting the backward movement of the plunger or piston, and at the same time functioning as guides for the flaps 25 to prevent the plunger from turning.

In the embodiment of FIGS. 3 to 10, the plunger has on one of the flaps 25, a seat 39 immediately adjacent a disk 31 which supports the piston 27. The seat 39 contains a blade or knife 43. Tip 21 carries a needle for the injection of the solution. FIG. 3 illustrates a deepened groove or step 52 instead of punctured portion 24. On aspiration of the plunger the knife 43 eventually enters said step 52. However, this embodiment can also have punctured portion or slot 24, as shown in FIG. 2. By pushing the plunger of the flaps 25 and pushing the circular disk 26, one will allow the blade 43, which is positioned in deepened groove or step 52 or extending through slot 24, to cut open the weakened section 23, destroying the cylinder 20 and making it impossible for the syringe to be used again.

Figure 4:
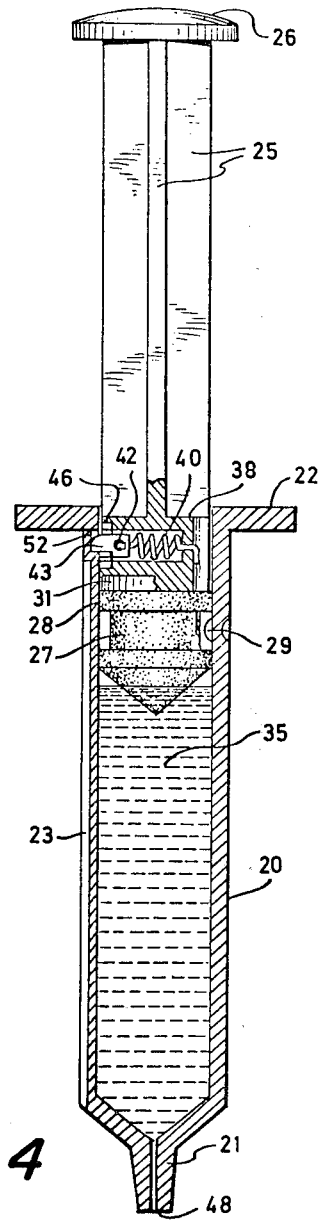
FIG. 4 is a conventional cross-sectional view corresponding to the embodiment illustrated in FIG. 3, after having extracted the plunger and filled the disposable syringe with injectable solution.
Figure 5:
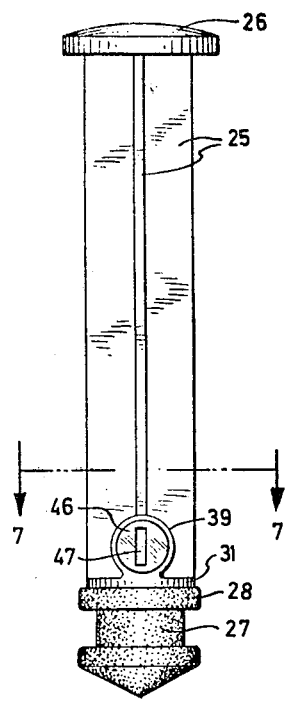
FIG. 5 is an elevational view of the plunger of the embodiment illustrated in FIGS. 3 and 4.
Figure 6:
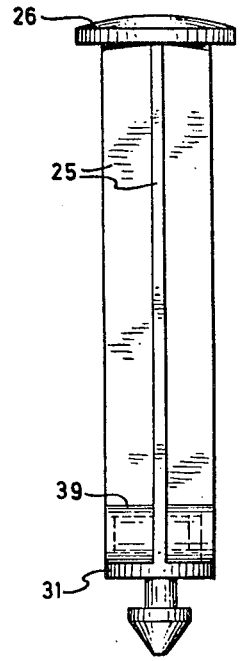
FIG. 6 is a top elevational view similar to FIG. 5, turned 90° in relation to the longitudinal axis of the plunger, without the cap which forms the piston of the syringe.
Figure 7:
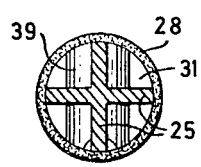
FIG. 7 is a side sectional view of 7—7 in FIG. 5.
Figure 8:
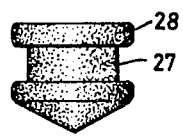
FIG. 8 is a top elevational view of the cap which makes up the piston of the syringe on a model of the same.

As may be seen in FIGS. 3 and 4, this plunger disk 31 of piston 27 and the seat 39 have a recess 38 which allows them to pass over the aforementioned stop 29.

Figure 9:
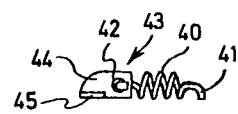
FIG. 9 is a top elevational view of the blade and spring corresponding to the embodiment, shown in FIGS. 3 and 4.
Figure 10:
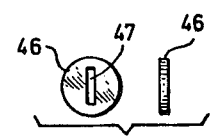
FIG. 10 is a side plan elevational view of the slotted cover of the seat contiguous with the supporting disk of the piston of the syringe in the inside of which is located the spring and cutting blade illustrated in FIG. 9.

In this embodiment, the plunger, which is made up of the flaps 25, has in the section adjacent to disk 31, a seat, preferably tubular, 39 which provides a housing transverse to the longitudinal axis of the plunger and inside of which there is a spring 40, which has one extreme end of the same 41 hooked to the base wall of the seat 39 and the other extreme end 42 hooked to the blade 43, said blade 43 being clearly shown in FIG. 9 and which has a rounded backside 44 and a straight front side with a cutting edge 45; said blade runs across a cover 46, of which is clearly shown in FIG. 10, and said cover 46 closes the aforementioned seat 39, and has been stated above, said cover 46 is perpendicular in the slot 47 to the blade 43. Said slot 47 is just a little wider than the width of the blade 43 which gives it a little clearance with the blade, and therefore when the plunger which is formed by the flaps 25, for the purpose of filling the syringe with a solution, the blade moves slightly in the direction of the cylinder along the rounded edge 44, which does not produce any cutting acton whatsoever along the wall of the cylinder. To the contrary, if it is desired to inject the solution, said blade 43 will move along the entire length of the slot 47 inside cover 46 up to the widest open position of the piston 27, contacting the wall of the cylinder with the cutting edge 45, and cutting, in this case, the said cylinder 20 through said slot or weakened section, destroying the syringe and making further use of it impossible. The slot 47, which lies in a plane passing through the central axis of the piston rod (said axis passing through the center of the cross formed by flaps 25, shown in FIG. 7), causes the blade 43 to remain in said plane passing through the central axis of the piston rod.

In this embodiment it may be clearly observed that the blade does not have to reach the end of its movement and protrude through slot 24, at the end of the tapered section 23 in order to cut the cylinder inasmuch as the play of the blade makes it possible to cut the cylinder in any position along the path of the movement of the piston, preventing the user from using the syringe several times, provided that the piston does not reach its most open position, which is to say, that in this embodiment of the invention, the blade will cut in any position of the same provided that the plunger is moved forward, meaning to say, injecting the solution which had previously been introduced into the syringe. Of course, if said blade reached slot 24, allowing the blade to cross said slot, the cutting would be faster and easier inasmuch as this is the ideal position for the cutting, as is shown in FIG. 4; for the introduction of the plunger into the assembly of this model of the syringe, a thin sheet is used, placing it between the inside wall of the cylinder 20 and the blade 43 in order to prevent the cutting of the wall of the cylinder. Once the piston reaches the end of its movement near the pivot of the syringe, the thin sheet is removed (not shown in the drawings), inasmuch as it properly belongs to the assembly and manufacture of said syringe.

In the embodiment of FIG. 2 in which blade 43' is integral to a plate 53 which is perpendicular to the same, positioned for transverse movement in cut 55 of one flap 25 of the plunger immediately adjacent to disk 31 which supports piston 27 and is pushed against the wall of the cylinder 20 by means of the action of a spring 54 fixed to the bottom wall of cut 55 behind said plate 53. Said cut 55 also provides a transversely extending housing. The blade 43' is guided against the wall of the cylinder 20 by a slotted plate 56 which is located over cut 55 of the flap 25. Once the piston 27 is extended out to its uppermost position, filling the syringe with an injectable solution, the spring 54 pushes blade 43' into a deepened groove 52 or a punctured portion 24, similar to the process outlined for the embodiment described above for FIGS. 3 to 10, as shown by the dotted lines shown in said FIG. 2, and in which case, when the solution is injected into the patient, the wall of the cylinder 20 is cut through a slot or weakened section 23 of the same, destroying the syringe and preventing any further use of the same. All of the other structural elements of this embodiment of the syringe are identical to those of the foregoing embodiment. The location of the mounting for knife 43' in cut 55 of the flap 25 of the piston rod as shown in the embodiment of FIG. 2, is such as to cause knife 43' to move radially with respect to the central axis of the piston rod and in this way most effectively cut the half-groove weakening 23. The slotted plate 56 serves as a guide means for the knife 43' so as to maintain said knife in a plane passing through the axis of the cylinder.

All of the above embodiments may be used with conventional needles which would seem to imply that a contaminated needle might be used with them. For this reason, a needle which can be used only once has been thought of, which is to say, that at the same time that the syringe is destroyed it would not be possible to use the contaminated needle in another standard syringe, or that a conventional needle may be used in the following embodiments of the invention.

FIGS. 11 and 12 show an embodiment of a needle which is applied principally to the empty disposable syringes already mentioned and which is integral to the cylinder 20 of the syringe; this needle 57 is made up of a puncturing portion 58, integral to a skirt 59, which embeds itself in the material of which the cylinder 20 is made in the molding process of the same.

FIG. 11 shows a sheath or protective covering 60 to prevent contamination or deterioration of said needle 57 before it is used.

Even through the above description has been directed to specific embodiments of this invention, it is to be understood by all skilled in the art, that any change in the form and detail shall be included within the field and scope of the same.

I claim:

1. A disposable syringe which renders itself non-reusable, which comprises a rigid cylinder coupled at one end to a bottom wall with an opening for the exit of the solution to be injected, and having the other end open, said end being integrally coupled to support flanges which extend outwardly and perpendicularly to the axis of the cylinder, and a plunger with a piston at the extreme end coupled to the cylinder, and a circular disk positioned on said plunger so as to permit sliding and moving of said plunger within said cylinder, wherein the cylinder has a longitudinal groove partially penetrating the wall of said cylinder and adjacent said partially penetrating groove a longitudinally extending section of the wall penetrable by a knife, said plunger having flaps extending outwardly of the axis of said plunger, there being a support disk of a semi-rigid piston at the extreme end opposite the circular disk, one of said flaps being oppositely aligned with the weakening groove of the cylinder, there being a recess in said flap immediately adjacent said support disk of said piston, said recess providing a transversely extending housing, there being a compressible spring having one of its ends attached to the wall of said housing and a cutting blade in said housing fixed to the other end of said compressible spring, said cutting blade being guided by a cover of said housing having a slot with a width slightly greater than the thickness of said blade, whereby to prevent twisting of said blade, said cutting blade being positioned so that upon injection of a solution, said weakened groove of the wall is cut along the length thereof as the injection proceeds, said cylinder having guide means for one of said flaps other than one which contains said blade to prevent rotation of the piston rod about its axis.

2. Disposable syringe according to claim 1, in which said blade has a rounded edge along the side most remote from said piston and a cutting edge along the edge closest the piston.

3. A disposable syringe according to claim 1, in which the cover is a slotted plate attached to a stepped portion made in the cut recess of the flap.

4. A disposable syringe according to claim 1, wherein there is a skirted needle embedded in the bottom wall of the cylinder.

5. A disposable syringe according to claim 1, in which the longitudinally extending section of the wall penetrable by a knife is a slot which entirely penetrates the wall of the cylinder.

6. A disposable syringe according to claim 1, in which the longitudinally extending section of the wall penetrable by a knife is a groove partially penetrating said wall.

* * * * *